(12) United States Patent
Klaue (10) Patent No.: US 12,137,950 B2
(45) Date of Patent: Nov. 12, 2024

(54) BONE NAIL

(71) Applicant: Kaj Klaue, Lugano (CH)

(72) Inventor: Kaj Klaue, Lugano (CH)

(*) Notice: Subject to any disclaimer, the term of this patent is extended or adjusted under 35 U.S.C. 154(b) by 0 days.

(21) Appl. No.: 17/766,596

(22) PCT Filed: Sep. 17, 2020

(86) PCT No.: PCT/CH2020/000013
§ 371 (c)(1),
(2) Date: Apr. 5, 2022

(87) PCT Pub. No.: WO2021/068088
PCT Pub. Date: Apr. 15, 2021

(65) Prior Publication Data
US 2023/0285059 A1     Sep. 14, 2023

(30) Foreign Application Priority Data
Oct. 9, 2019 (CH) .................... 1290/19

(51) Int. Cl.
*A61B 17/72* (2006.01)
*A61B 17/86* (2006.01)

(52) U.S. Cl.
CPC ........ *A61B 17/7291* (2013.01); *A61B 17/725* (2013.01); *A61B 17/7283* (2013.01); *A61B 17/8605* (2013.01)

(58) Field of Classification Search
CPC .............. A61B 17/725; A61B 17/7291; A61B 17/8605
See application file for complete search history.

(56) References Cited

U.S. PATENT DOCUMENTS

| | | | | |
|---|---|---|---|---|
| 3,474,537 A | * | 10/1969 | Christensen | A61C 8/0009 433/174 |
| 4,011,863 A | * | 3/1977 | Zickel | A61B 17/7208 606/62 |
| 5,454,813 A | * | 10/1995 | Lawes | A61B 17/1721 606/62 |
| 5,505,731 A | * | 4/1996 | Tornier | A61B 17/7055 606/261 |
| 5,534,027 A | * | 7/1996 | Hodorek | A61B 17/8047 606/295 |

(Continued)

FOREIGN PATENT DOCUMENTS

| | | |
|---|---|---|
| DE | 4343117 A1 | 6/1995 |
| DE | 102005042766 B4 | 1/2007 |

(Continued)

OTHER PUBLICATIONS

International Search Report dated Mar. 5, 2021 filed in PCT/CH2020/000013.

*Primary Examiner* — David W Bates
(74) *Attorney, Agent, or Firm* — Rankin, Hill & Clark LLP (57) ABSTRACT

Bone nail (1) with a front portion (2), suitable for insertion into the bone and having a free end (3), a rear portion (5) having a free end (6), an outer surface (4); and a nail axis (7); wherein the rear portion (5) has a through hole (8) with a central axis (12) and with an inlet opening (9) located at the rear free end (6) and an outlet opening (10) located on the outer surface (4) of the rear section (5) whereby the through hole (8) is formed for receiving a polyaxial bone screw (11).

22 Claims, 6 Drawing Sheets

(56) References Cited

U.S. PATENT DOCUMENTS

| | | | | | |
|---|---|---|---|---|---|
| 5,549,610 | A | * | 8/1996 | Russell | A61B 17/72 606/62 |
| 5,743,908 | A | * | 4/1998 | Kim | A61B 17/7225 606/916 |
| 5,984,681 | A | * | 11/1999 | Huang | A61C 8/0009 433/173 |
| 6,221,074 | B1 | * | 4/2001 | Cole | A61B 17/72 606/62 |
| 6,270,499 | B1 | * | 8/2001 | Leu | A61B 17/725 606/62 |
| 6,322,562 | B1 | * | 11/2001 | Wolter | A61B 17/7258 606/291 |
| 6,443,954 | B1 | * | 9/2002 | Bramlet | A61B 17/744 606/328 |
| 6,629,976 | B1 | * | 10/2003 | Gnos | A61B 17/7291 606/62 |
| 6,706,073 | B2 | * | 3/2004 | Draenert | A61F 2/4607 623/23.26 |
| 7,524,326 | B2 | * | 4/2009 | Dierks | A61B 17/7041 606/308 |
| 8,187,276 | B1 | * | 5/2012 | Zahiri | A61B 17/68 606/65 |
| 8,303,589 | B2 | * | 11/2012 | Tyber | A61B 17/864 606/301 |
| 8,986,353 | B2 | * | 3/2015 | Johnson | A61B 17/1728 606/287 |
| 9,044,282 | B2 | * | 6/2015 | Tyber | A61B 17/1775 |
| 10,898,248 | B2 | * | 1/2021 | Cundiff | A61F 2/30 |
| 11,344,349 | B2 | * | 5/2022 | Fessler | A61B 17/7037 |
| 2002/0133156 | A1 | * | 9/2002 | Cole | A61B 17/725 606/62 |
| 2004/0049192 | A1 | * | 3/2004 | Shimizu | A61B 17/7266 606/62 |
| 2005/0165400 | A1 | * | 7/2005 | Fernandez | A61B 17/8057 606/291 |
| 2006/0015101 | A1 | * | 1/2006 | Warburton | A61B 17/1668 606/62 |
| 2006/0189991 | A1 | * | 8/2006 | Bickley | A61F 2/0811 623/13.12 |
| 2008/0015593 | A1 | * | 1/2008 | Pfefferle | A61B 17/8052 606/282 |
| 2010/0145397 | A1 | * | 6/2010 | Overes | A61B 17/8038 606/319 |
| 2010/0292722 | A1 | | 11/2010 | Klaue | |
| 2010/0324556 | A1 | | 12/2010 | Tyber et al. | |
| 2011/0022066 | A1 | * | 1/2011 | Sevrain | A61B 17/86 606/151 |
| 2011/0184470 | A1 | * | 7/2011 | Gorek | A61B 17/7011 606/279 |
| 2011/0282398 | A1 | * | 11/2011 | Overes | A61B 17/8877 606/310 |
| 2014/0066932 | A1 | * | 3/2014 | Appenzeller | A61B 17/72 606/64 |
| 2014/0142575 | A1 | | 5/2014 | Biedermann et al. | |
| 2015/0342650 | A1 | * | 12/2015 | Schreiber | A61B 17/7241 606/64 |
| 2016/0128732 | A1 | * | 5/2016 | Strnad | A61B 17/7034 606/267 |
| 2018/0271567 | A1 | * | 9/2018 | Schumacher | A61B 17/725 |
| 2019/0336189 | A1 | * | 11/2019 | Cundiff | A61F 2/30 |

FOREIGN PATENT DOCUMENTS

| | | |
|---|---|---|
| EP | 2732783 A1 | 5/2014 |
| WO | 2005092219 A1 | 10/2005 |
| WO | 2014035811 A1 | 3/2014 |

* cited by examiner

BONE NAIL

BACKGROUND OF THE INVENTION

1. Field of the Invention

The invention relates to a bone nail, to a bone screw for use with the bone nail, to a construct comprised of a bone nail and a bone screw and to a kit including a plurality of bone nails and a plurality of bone screws.

2. Description of the Related Art

A bone nail for the hind foot is known from document US 2014/142575 A1. An arched bone nail for the hind foot is proposed which extends from an axial surface of the calcaneus in a nearly circular shape through the talus into the tibia. The bone nail is curved and has a radius of curvature of at least 130 mm. At least one transverse bore hole for receiving a locking screw is provided along the length of the nail, and at a rear end, an inclined bore hole extends from the rear end to lock the bone nail with a bone screw in the calcaneus and talus to allow for neutralizing forces that tend to loosen the nail and for fixing the subtalar joint. The corresponding bone screw has a shank and a head, wherein the shank between the tip of the screw and the head is holding a thread. Furthermore, this bone screw is designed as an angularly stable locking screw, i.e. by tightening the screw, an angle-stable nail-screw connection is achieved. A disadvantage of these known nails for osteosynthesis of bone is a lack of possibility for polyaxial fixation of bone screws in these bone nails. So far screws can be screwed into nails for osteosynthesis only at a predetermined angle. If plates are used to fix bone fractures, screws can be inserted polyaxially and with stable angles. Examples of this are disclosed in DE 43 43 117 A1 and DE 10 2005 042 766 B4. Transfer of these quoted and known devices for plate osteosyntheses on nail osteosyntheses is not possible because screw heads for plates apply plates onto the surface of a bone. In contrast, screws for nails are applied to interlock the nail within the bone. Since a nail lock is located within the bone and not on the surface of the bone, a bone screw used to fix a bone plate cannot be used for a polyaxial angular locking of a bone nail.

The chronology of using the fixation by nail and screw is imperative: first the nail is introduced. Second the screw is introduced crossing and seating within the nail. The nail cannot be twisted or turned without losing significant stability within the bone (form-fit). The surgeon needs a two-dimensional liberty in choosing the orientation of the screw within the sagittal and the coronal planes which is not possible in the state of the art.

BRIEF SUMMARY OF THE INVENTION

It is an object of the invention to remedy this situation. The invention has for its object to provide a bone nail with a polyaxial angular stable lockable receptacle for a bone screw.

The invention solves the posed problem with a bone nail as disclosed and claimed herein, with a bone screw as disclosed and claimed herein, with a construct as disclosed and claimed herein and with a kit as disclosed and claimed herein.

The advantages achieved by the invention are essentially to be seen in the fact that thanks to the bone nail according to the invention:

- a polyaxial angle stable nail-screw connection can be made with standardized bone screws provided with a spherical screw head;
- devices previously known in the prior art have only screws that allow for each hole only a single axis direction. In contrast, the bone nail according to the invention allows for the realization of three different functions: as a set or positioning screw, lag screw or as a locked screw; as a set screw, the screw holds a thread on its whole length. As a lag screw, the screw holds a thread on its tip only, in this case on a length of <30 mm and as locked screw, the screw (and the nail) cannot back-up
- the polyaxially angle stable nail-screw connection allows for adapting the actual angle between the axis of the bone nail at the free end of the posterior portion and the central axis of the bone screw. Such adaptation is required due to the singular orientation of the bones about the hindfoot in relation to the axis of the bone nail.

Further advantageous embodiments of the invention can be commented as follows:

In a special embodiment, the through-hole is designed such that a polyaxial bone screw can be introduced within a circular cone with a central axis and a half cone angle of 15°.

In a further embodiment, the central axis of the through hole runs coaxially or tangentially to the nail axis.

In yet another embodiment, the central axis of the through hole and the nail axis form an angle, measured at the free end of the rear portion of the nail of at most 25°, preferably at most 15°. For nails having a curved axis the angle is measured between the tangent to the curved axis and the central axis of the through hole.

In another embodiment, the rear portion of the nail is fully formed except for the through-hole.

In another embodiment, the front portion is partially or completely hollow.

In another embodiment, the cross section of the bone nail tapers in sections or over the entire length of the bone nail from back to front, preferably conically.

In another embodiment, the cross section decreases from back to front in sections or over the entire length of the bone nail per mm length by 0.076 to 0.100 mm$^2$.

In yet another embodiment, the front portion has a slot.

In a further embodiment, the curved nail axis has a radius of curvature of 100 mm to 400 mm.

In another embodiment, the curved nail axis has a radius of curvature of less than 140 mm, preferably less than 130 mm.

In a further embodiment, the rear portion has a length of 110 to 150 mm.

In yet another embodiment, the central axis lies within the same plane E, which is spanned by the curved nail axis.

In another embodiment, the central axis intersects the plane E, which is spanned by the curved central axis, at an angle of at most 5°, preferably at most 2°.

In another embodiment, the through hole has an internal thread.

In another embodiment, the outer surface of the bone nail has a structuring, which is preferably provided with at least one longitudinally extending rib or groove.

In another embodiment, the structuring increases the surface of the unstructured bone nail 1.3 to 2.7 times, preferably 1.6 to 2.4 times.

In a further embodiment, with a plurality of ribs or grooves, the distance therebetween is in the range of 2 to 8 mm, preferably in the range of 3 to 6 mm.

In a further embodiment, the depth of the grooves, or the height of the ribs is at least 1 mm, preferably at least 2 mm.

In another embodiment, the rear portion is stiffer than the front portion.

In another embodiment, a polyaxial bone screw within an elliptical cone is insertable therein, wherein the cone angle measured in the plane defined by the curved nail axis E is greater than when measured perpendicular to this plane.

In yet another embodiment, the half cone angle measured in the plane E is in the range of 7.5°-15° and the half cone angle measured perpendicularly thereto is in the range of 5°-10°.

In a further embodiment the bone nail has the length L and that outlet opening is extending not more than 0.25 L, preferably not more than 0.30 L towards the rear free end.

In a further embodiment the through hole has a mean cross-sectional area in the range of 200 mm² to 400 mm².

In a further embodiment the bone nail has a volume $V_N$ and the through hole has a volume $V_H$ in the range 0.06 $V_N$ to 0.16 $V_N$, preferably in the range of 0.080 $V_N$ to 0.125 $V_N$.

Still in a further embodiment the outlet opening of the through hole has an area of $A_o$ and the inlet opening of the through hole—which is intended for receiving the head of a bone screw—has an area of $A_i$ and that the relation $A_o > A_i$ is valid, preferably $A_o > 2A_i$.

In a further embodiment the bone nail has a front portion 2 which is deformable, preferably elastically deformable.

The deformable front portion—measured from the free end of the nail—purposefully runs over at most 50% of the total length of the bone nail, preferably at most 35%.

The deformable front portion—measured from the free end—runs purposefully at minimum over 10% of the total length of the bone nail (1), preferably over 25% at minimum.

In a further embodiment the deformable front portion of the bone nail increases, preferably gradually, in elasticity towards to the free end of the nail.

According to another aspect of the invention, there is provided a bone screw suitable for insertion into the through-hole of the bone nail, the bone screw having a conical or spherical screw head allowing for a polyaxial anchoring at the bottom of the through-hole within a target cone of half the cone angle of 10°.

In a further embodiment of the bone screw, the conical screw head has a thread.

In another embodiment, the spherical screw head has a smooth outer surface and is axially blocked by means of a threaded cap in the through-hole.

In another embodiment the polyaxial bone screw has a length in the range of 50 mm to 100 mm, preferably of 65 mm to 80 mm.

In a further embodiment the bone screw is a hollow screw so that it is possible to introduce a Kirschner wire for orientation of the screw.

According to another aspect of the invention, a construct consisting of a bone nail and a bone screw is provided, both being made of the same material, preferably titanium or a titanium alloy.

In a special embodiment the through hole of the bone nail at its inlet opening is formed in such a way that it is able to fully receive the head of the polyaxial bone screw.

In a further embodiment the length $L_T$ of the through hole (8) and the length $L_s$ of the bone screw (11) show the relation $L_s > L_T$ and preferably $L_s > 2 L_T$.

In a further embodiment the construct is intended for the fixation of subtalar arthrodesis.

In yet another aspect of the invention, a kit comprising a plurality of bone nails and a plurality of bone screws is provided.

In a special embodiment of the kit, the latter additionally comprises a threaded cap for the axial blocking of the screw head.

A preferred application of the bone nail according to the invention is used for the fixation of isolated subtalar arthrodesis.

All defined embodiments of the polyaxial screw are applicable to a nail presenting a curvature with an infinite radius by means of a straight nail.

A BRIEF DESCRIPTION OF THE DRAWINGS

Several embodiments of the invention will be described in the following by way of schematic drawings and examples in which.

DETAILED DESCRIPTION OF THE INVENTION

Figure 1:
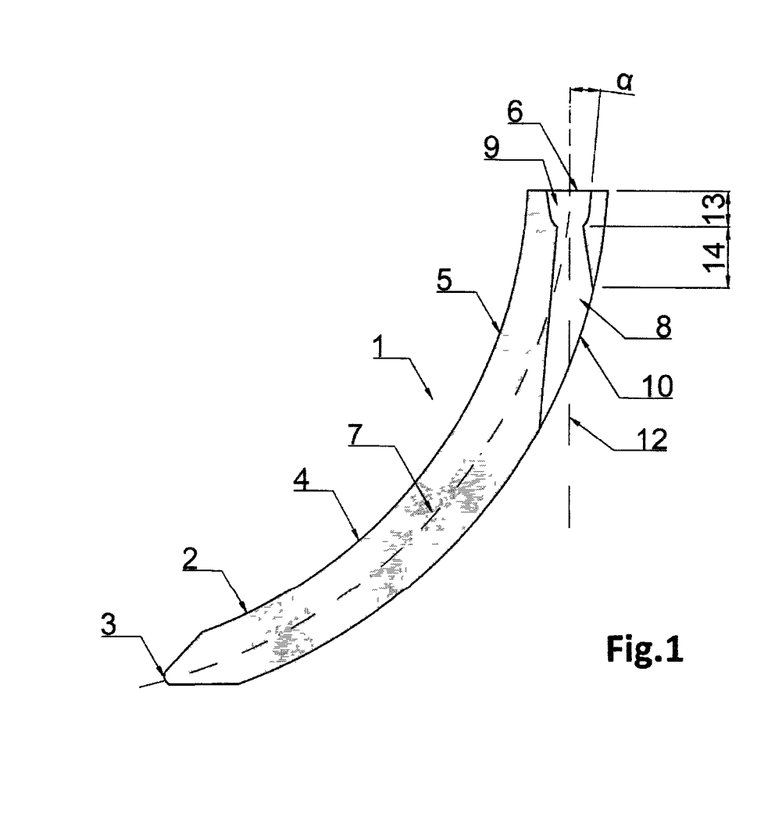
FIG. 1 illustrates a side view of a first embodiment of the bone nail according to the invention.

The embodiment of the bone nail 1 according to the invention as illustrated in FIG. 1 comprises substantially a front portion 2 with a free end 3, a rear portion 5 with a free end 6 and an outer surface 4, wherein the rear portion 5 has a through hole 8 with a central axis 12 and comprises an inlet opening 9 located at the rear free end 6 and an outlet opening 10 located at the outer surface 4 of the rear section 5. The bone nail 1 also has a curved axis 7 and tapers down from the rear free end 6 to the front free end 3 in cross-section. The through-hole 8 is designed to receive a polyaxial bone screw 11.

For this purpose, the through-hole 8 tapers from the free end 6 of the rear portion 5 in the form of a first truncated cone 13 to a minimum diameter for passing the threaded shank of a bone screw 11 and then widens in the form of a second truncated cone 14 against the outer surface 4 of the rear portion 5 thus forming the outlet opening 10. The first truncated cone 13 and the second truncated cone 14 have a circular cross-section and—by way of example and not limitation—form in relation to the central axis 12 a half-cone angle $\alpha=\beta$ of 7.5 to 10 degrees °, so that insertion of a polyaxial bone screw 11 within a circular cone is made possible. Further, the central axis 12 of the through hole 8 lies in the plane E, which is spanned by the curved axis 7 of the bone nail 1.

In alternative embodiments of the bone nail 1, the through-hole 8 is formed such that the first truncated cone 13 and the second truncated cone 14 have an elliptical cross section, so that a polyaxial bone screw 11 within an elliptical cone can be inserted therein, wherein the cone angle $\alpha=\beta$ measured within the plane E spanned by the curved axis 7 of the nail 1 is greater than when measured perpendicular to this plane. By way of example, the half cone angle $\alpha'=\beta'$ measured in the plane E lies in the range of 10° and the half cone angle $\alpha''=\beta''$ measured perpendicularly thereto lies in the range of 7.5°. However, further embodiments of the bone nail 1 allow through holes 8, which measure in the plane E a half cone angle $\alpha'=\beta'$ at most 15° and perpendicular thereto a half cone angle $\alpha''=\beta''$ at most 10°.

The central axis 12 of the through hole 8 is rectilinear and extends at the free end 6 of the rear portion tangential to the axis 7 of the bone nail. 1

The free end 3 of the front portion 2 is formed as a rounded tip, so that it is suitable for insertion into the bone. The rear portion 5 of the bone nail 1 is fully formed apart from the through hole 8.

The cross-section of the bone nail 1 narrows, by way of example and not limitation, conically over the entire length of the bone nail 1 from the free end 6 of the rear portion 5 to the free end 3 of the front portion, wherein the cross-sectional area from back to front over the entire length of the bone nail 1 is reduced per mm length by 0.100 mm².

Further embodiments allow a partial tapering of the bone nail 1 from back to front, whereby the cross section decreases from back to front in sections per mm length by 0.076 to 0.100 mm².

With regard to the radius of curvature of the axis 7 of the bone nail 1, it may be noted that, according to other embodiments, the radii of curvature may vary along the axis 7. In this specific embodiment, the radius of curvature is 200 mm. However, further embodiments of a bone nail allow radii of curvature of at least 100 mm, others of at least 140 mm, still others of at least 150 mm and, according to most specific embodiments, of at least 190 mm or at least 200 mm. The geometry chosen depends on the specific conditions that are individual to each patient. Likewise, upper limits of the radius of curvature can be infinite and thus correspond to a straight nail.

The length of the bone nail is advantageously at least 110 mm. Preferably, the length of the bone nail is at most 250 mm. The length of the rear portion 5 (stiff) of the bone nail 1, measured from the rear end 5, is 110 mm. According to other embodiments, the length for the rear portion 5 of the bone nail 1 may be 125 mm or 150 mm.

The diameter of bone nail is advantageously at least 10 mm. Preferably, the diameter of the bone nail is at most 11 mm.

Figure 2:
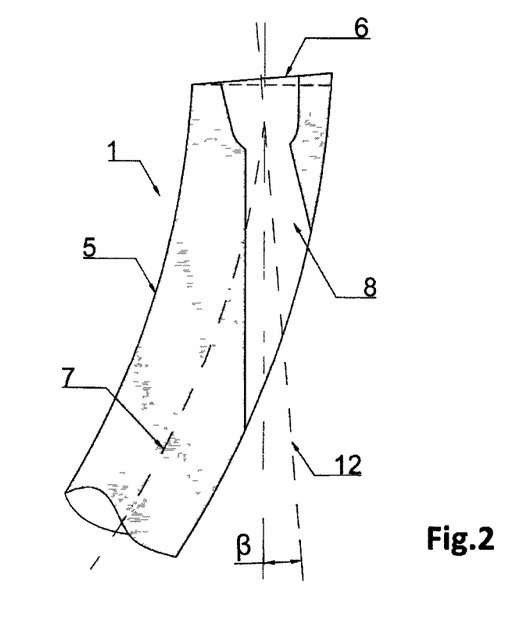
FIG. 2 illustrates a longitudinal section through the rear section of a second embodiment of the bone nail according to the invention.
Figure 6:
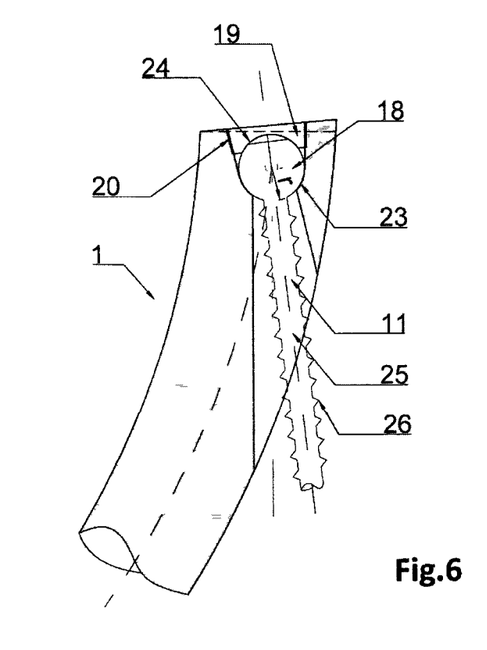
FIG. 6 illustrates a longitudinal section through the rear portion of the embodiment of the bone nail according to the invention shown in FIG. 2 with inserted bone screw and threaded cap.

In FIG. 2 an alternative embodiment of the bone nail 1 is illustrated, which differs from FIG. 1 only in that the angle β between the central axis 12 of the through hole 8 at the free end 6 of the rear portion 5 and the axis 7 of the bone nail 1, by way of example and not limitation, measures 7.5°. However, other embodiments allow for an angle β between the central axis 12 of the through hole 8 and the axis 7 of the bone nail 1, measured at the free end 6 of the rear portion 5, of at most 10° In FIGS. 3 and 6, the bone nail 1 according to FIG. 2 together with a bone screw 11 is shown. The bone screw 11 comprises a shank 25 with a thread 26 and has a spherical screw head 18 with a radius r, allowing polyaxial anchoring in the through-hole 8 within a target cone with the half cone angle of 7.5°. The spherical screw head 18 has a smooth outer surface and is located at the end of the semi-conical opening (first truncated cone 13) on a concave support surface 23, which corresponds exactly to the outer dimensions of the screw head, in particular the radius r of the screw head 18 (form fit). The thus positioned screw head 18 is axially blocked by means of a threaded cap 19 in the through hole 8 (FIG. 6). The threaded cap 19 comprises a spherical recess 24 for partially receiving the spherical screw head 18, wherein the spherical recess 24 has the same radius r as the spherical screw head 18 in order to produce a form fit here as well. For this purpose, the through hole 8 is provided with an internal thread 20, which allows the screwing of the threaded cap 19. Within the elliptical cone, the circular thread for fixing the cap is engraved within the smallest diameter of the elliptical cone.

In an alternative embodiment the shank 25 of the bone screw 11 comprises a smooth circular portion between the screw head 18 and the thread 26, which extends over a length of minimum 40 mm. (lag screw).

Figure 4:
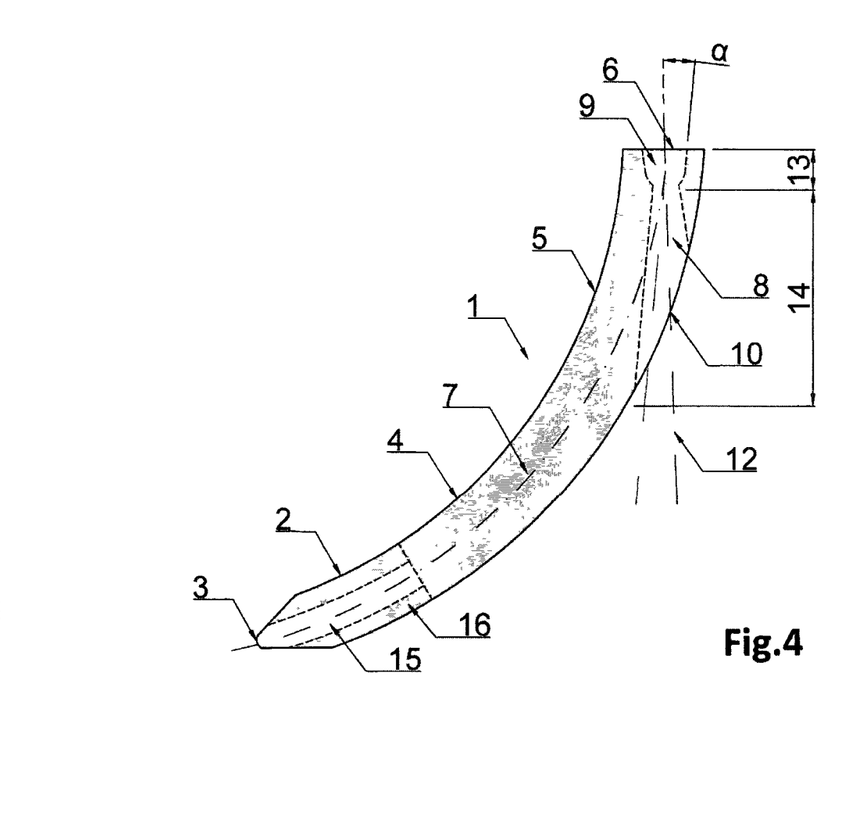
FIG. 4 illustrates a side view of a third embodiment of the bone nail according to the invention.

In FIG. 4, an embodiment of the bone nail 1 is shown, which differs from FIG. 1 only in that the front portion 2 is partially hollow and includes a central cavity 15 which is open at the free end 3 of the front portion 2. In addition, the front portion 2 of the bone nail 1 has a slot 16. The cavity 15 of the bone nail 1 in the front section 2 presents a thin-walled cross-sectional profile with a peripheral wall having a small wall thickness, which is also severed by the longitudinal slot 16 in the plane E defined by the curved axis 7. Due to the lower rigidity of the front part of section 2, this can deform during insertion into the tibia, so that the front portion 2 after implantation may have a significantly greater radius of curvature or even form a straight line.

Figure 5:
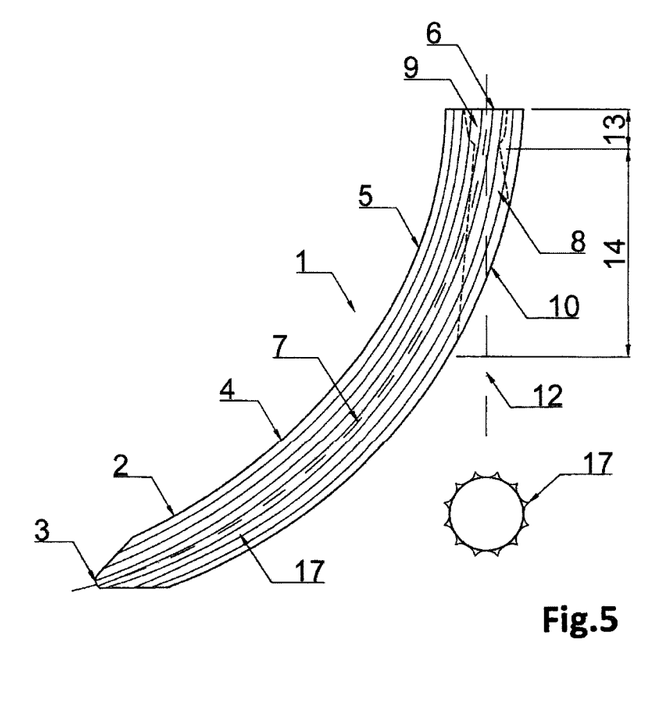
FIG. 5 illustrates a side view of a fourth embodiment of the bone nail according to the invention.

FIG. 5 shows an embodiment of the bone nail 1, which differs from FIG. 1 only in that the outer surface 4 of the bone nail 1 comprises a structure in the form of grooves 17, thereby forming a groove-rib pattern, wherein the grooves 17 are aligned parallel to the axis 7 in order to better guide the bone nail 1 when inserting it into the bony hole of the hind foot. This pattern further enlarges the surface and allows for improved integration of the bone nail 1 into the growing bone tissue surrounding the nail once ingrowth of bone into the grooves 17 has begun. Moreover, the groove rib pattern oriented in this direction allows a greater press fit during insertion while reducing the force required.

In various embodiments, the distance between the grooves 17, measure within the range of 2-8 mm, preferably in the range of 3-6 mm and the depth of the grooves 17 at least 1 mm, preferably at least 2 mm. By forming the grooves 17, in other embodiments, the surface of the unstructured bone nail 1 can be increased by 1.3 to 2.7 times, preferably by 1.6 to 2.4 times.

Figure 3:
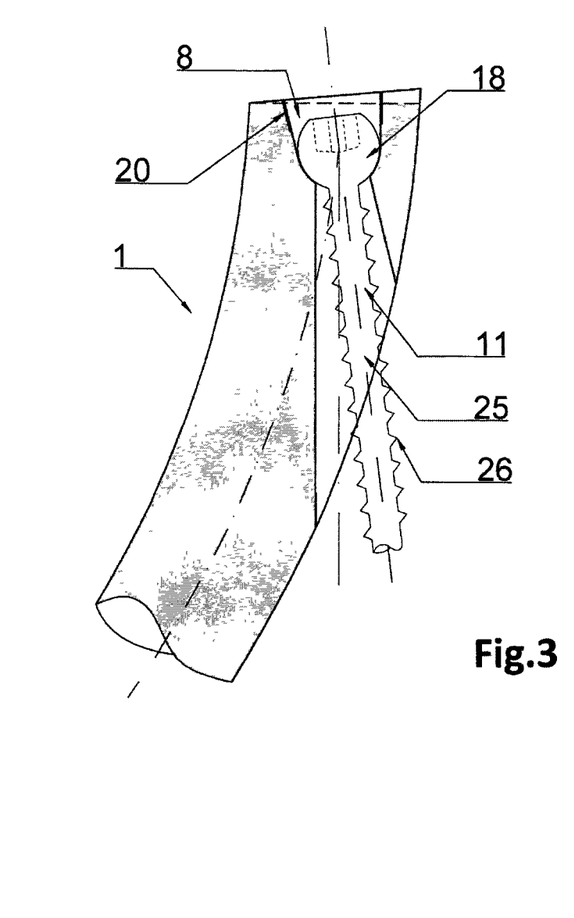
FIG. 3 illustrates a longitudinal section through the rear section of the embodiment of the bone nail according to the invention shown in FIG. 2 with inserted bone screw.
Figure 7:
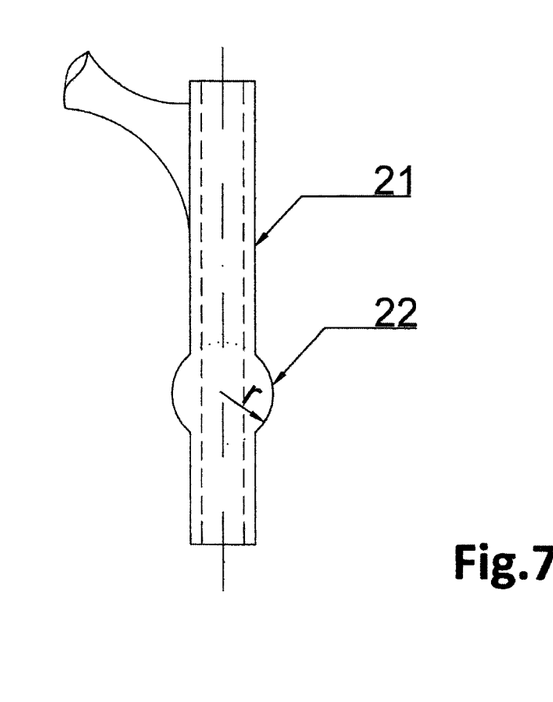
FIG. 7 illustrates a side view of an embodiment of the drill sleeve according to the invention.
Figure 8:
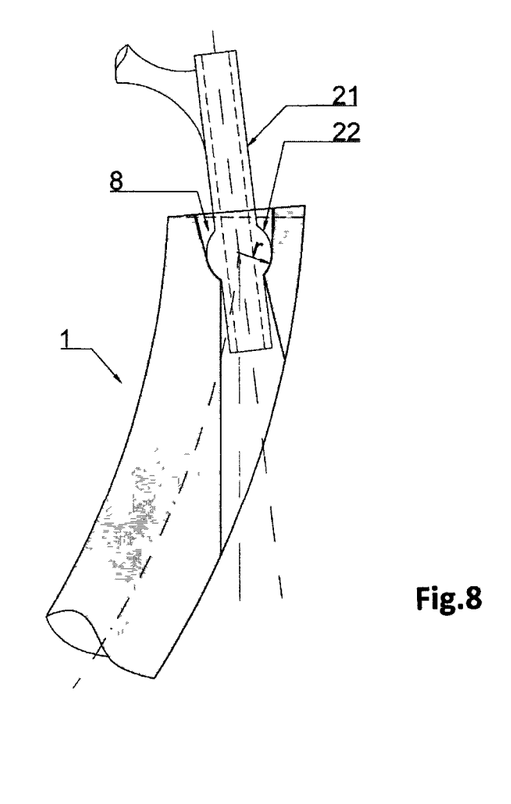
FIG. 8 illustrates a side view of the embodiment of the drill sleeve according to the invention shown in FIG. 7 introduced into the through-hole in the bone nail.

FIGS. 7 and 8 show an embodiment of a drill sleeve 21 according to the invention, which comprises a spherical section 22 with the same radius r as the spherical screw head 18 (FIG. 3). The drill sleeve 21 sits—like the later tightened bone screw 11—on the fitting support 23 and can be "balllike" pivoted in any direction to perform a targeted hole in the bone, which corresponds to the possibility of pivoting within the cone.

Figure 9:
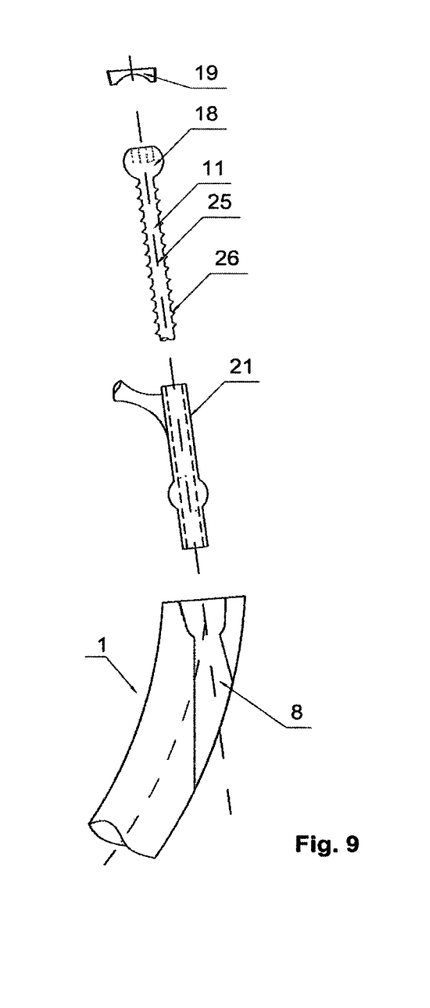
FIG. 9 illustrates the assembling of the nail, the drill sleeve, the screw and the locking cap according to the invention.

FIG. 9 illustrates the assembling of the nail 1 with the through hole 8, the drill sleeve 21, the bone screw 11 with head 18, shank 25 with thread 26, and the locking cap 19.

Figure 10:
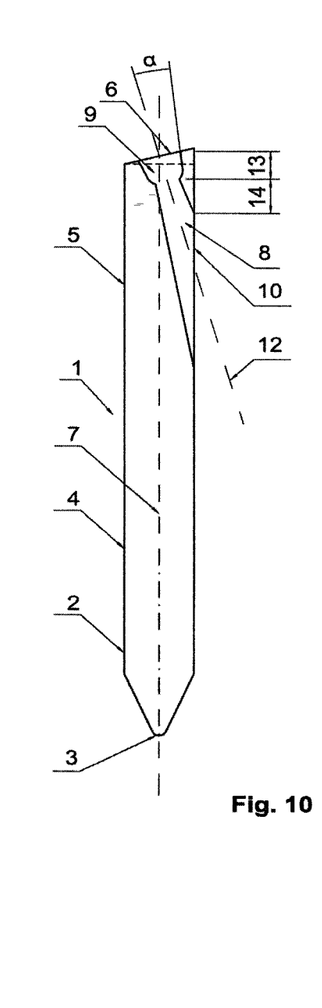
FIG. 10 illustrates a side view of an embodiment of the bone nail according to the invention including the infinite length of the radius of the curve (r=∞) in which the nail is straight.
Figure 11:
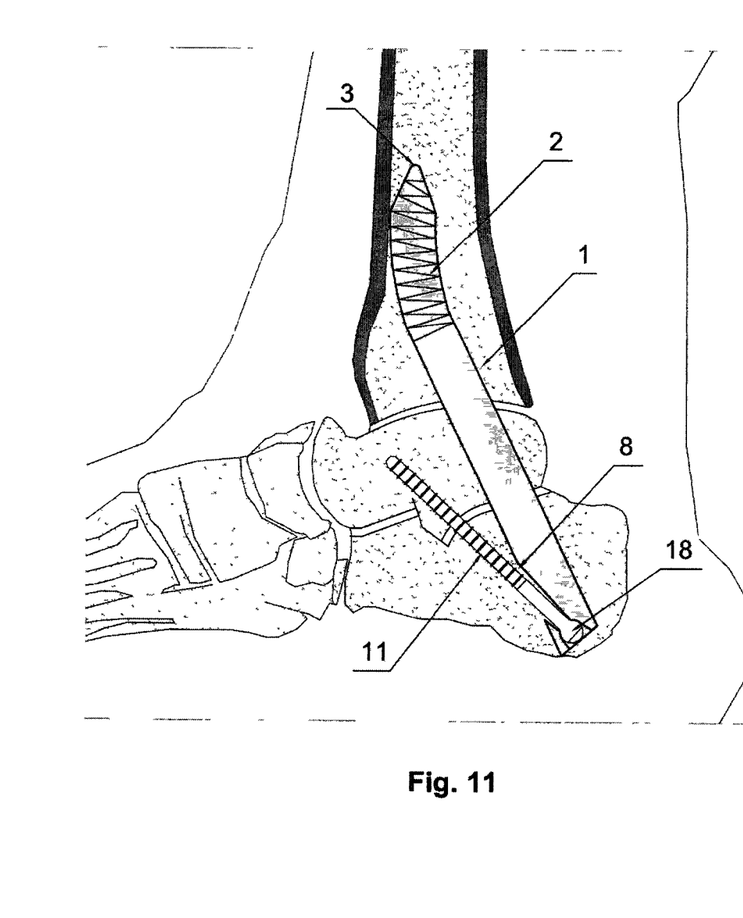
FIG. 11 illustrates through a schematic representation of a radiograph within the sagittal plane of a hindfoot on which the straight nail shown in FIG. 10 is introduced through an opening at the "Tuber calcanei".

FIG. 10 shows a straight bone nail 1 with a through hole 8 running at an angle α of 15° with respect to the nail axis 7. The inlet opening 9 is formed to receive the head of a bone screw and enlarges towards the outlet opening 10 conically so that a polyaxial screw can be placed at different angles with respect to the nail. In FIG. 11 the originally straight nail of FIG. 10 is shown in a schematic representation of a radiograph within the sagittal plane of a hindfoot after implantation of the nail. As can be seen the deformable front portion 2 of the nail 1 has adapted itself to the bone geometry and the bone screw 11 has been introduced through an opening at the "Tuber calcanei" and fixed in a desired orientation for optimal fixation of the construct.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

The invention claimed is:

1. A bone nail for use with a polyaxial bone screw having a screw head and a threaded shank, the bone nail comprising:
   a front portion configured for insertion into a bone, said front portion having a front free end;
   a rear portion having a rear free end;
   an outer surface; and
   a nail axis;
   wherein the outer surface of the bone nail is entirely unthreaded,
   wherein the rear portion of the bone nail includes a through hole defined by an inner surface,
   wherein an inlet opening of the through hole is located at the rear free end,
   wherein an outlet opening of the through hole is surrounded by the outer surface of the bone nail in the rear portion of the bone nail,
   wherein the through hole has a central axis,
   wherein, for the purpose of receiving said polyaxial bone screw in a selectable orientation, the inner surface that defines the through hole, beginning from the inlet opening at the rear free end, tapers in the form of a first truncated cone having an axis coincident with the central axis of the through hole, then includes a concave support surface for contacting the screw head of the polyaxial bone screw when the polyaxial bone screw is received in the through hole, then narrows to a minimum diameter for passage of the threaded shank of said polyaxial bone screw, and then widens in the form of a second truncated cone having an axis coincident with the central axis of the through hole until it reaches the outlet opening,
   wherein the central axis of the through hole forms with the nail axis, measured at the free end of the rear portion, an angle of at most 25°,
   wherein a cross section taken through the bone nail perpendicular to the nail axis at any point along its length defines, except for any longitudinally extending ribs or grooves that may be provided on or in the outer surface of the bone nail, a circle or an ellipse, except at the through hole,
   wherein a cross section taken through the first truncated cone perpendicular to its axis at any point along the length of the axis defines a circle or ellipse, and
   wherein a cross section taken through the second truncated cone perpendicular to its axis at any point along the length of the axis defines a circle or ellipse.

2. The bone nail according to claim 1, wherein the through hole is formed such that the polyaxial bone screw is insertable within a circular cone with the central axis and a half cone angle of 7.5°.

3. The bone nail according to claim 1, wherein the through hole is formed such that the polyaxial bone screw is insertable therein so as to include an angle α with the central axis of 0.0° to 7.5°.

4. The bone nail according to claim 1, wherein the rear portion is solidly formed except for the through hole.

5. The bone nail according to claim 1, wherein the front portion is partially or completely hollow.

6. The bone nail according to claim 1, wherein the outer surface of the bone nail tapers over part of its length from the rear portion to the front portion.

7. The bone nail according to claim 1, wherein the front portion has a slot.

8. The bone nail according to claim 1, wherein the central axis lies within a plane E, which includes the nail axis.

9. The bone nail according to claim 1, wherein the outer surface is provided with at least one longitudinally extending rib or groove.

10. The bone nail according to claim 1, wherein the rear portion is stiffer than the front portion.

11. The bone nail according to claim 1, wherein the front portion is deformable.

12. The bone nail according to claim 1, wherein the outer surface of the bone nail tapers over its entire length from the rear portion to the front portion.

13. The bone nail according to claim 1, wherein the nail axis is curved.

14. The bone nail according to claim 13, wherein the curved nail axis has radii of curvature that vary along the nail axis.

15. A combination comprising:
    a bone nail according to claim 1; and
    a polyaxial bone screw configured for insertion into the through-hole of the bone nail.

16. The combination according to claim 15, wherein the bone screw comprises:
    a conical or spherical screw head adapted for polyaxial anchoring in the through hole of the bone nail within a target cone with the half cone angle of 7.5°; and
    a shank with a thread.

17. The combination according to claim 15, wherein the bone screw is hollow.

18. The combination according to claim 15, wherein the inlet opening of the through hole of the bone nail is configured to fully receive the head of the polyaxial bone screw.

19. The combination according to claim 15, wherein the through hole has a length $L_T$ that is less than a length $L_s$ of the bone screw.

20. The combination according to claim 16, wherein the concave support surface for contacting the screw head corresponds to the outer surface of the screw head for establishing a form fit connection between the outer surface of the screw head and the concave support surface when the polyaxial bone screw is received in the through hole.

21. A kit comprising a plurality of bone nails according to claim 1 and a plurality of polyaxial bone screws.

22. The kit according to claim 21, wherein the kit further comprises threaded caps for axial blocking of screw heads of the polyaxial bone screws.

\* \* \* \* \*